(12) United States Patent
Futrell et al.

(10) Patent No.: US 9,596,994 B2
(45) Date of Patent: Mar. 21, 2017

(54) SYSTEM AND METHODS FOR ILLUMINATING MATERIALS (76) Inventors: J. William J. Futrell, Pittsburgh, PA (US); David J. Gaskin, Houston, TX (US)

(*) Notice: Subject to any disclaimer, the term of this patent is extended or adjusted under 35 U.S.C. 154(b) by 801 days.

(21) Appl. No.: 12/302,717

(22) PCT Filed: Jun. 4, 2007

(86) PCT No.: PCT/US2007/013157
§ 371 (c)(1),
(2), (4) Date: Aug. 25, 2009

(87) PCT Pub. No.: WO2007/143200
PCT Pub. Date: Dec. 13, 2007

(65) Prior Publication Data
US 2010/0016729 A1 Jan. 21, 2010

Related U.S. Application Data

(60) Provisional application No. 60/810,339, filed on Jun. 2, 2006.

(51) Int. Cl.
*A61B 6/00* (2006.01)
*A61B 5/00* (2006.01)
*A61B 5/20* (2006.01)
*A61B 5/06* (2006.01)

(52) U.S. Cl.
CPC .......... *A61B 5/0086* (2013.01); *A61B 5/0084* (2013.01); *A61B 5/064* (2013.01); *A61B 5/201* (2013.01); *A61B 5/4244* (2013.01); *A61B 5/06* (2013.01); *A61B 90/30* (2016.02)

(58) Field of Classification Search
CPC . A61B 5/0084; A61B 5/0086; A61B 5/14546; A61B 5/6848; A61B 5/6882
USPC ............... 600/407, 473, 476, 477, 310, 181
See application file for complete search history.

(56) References Cited

U.S. PATENT DOCUMENTS

| | | | |
|---|---|---|---|
| 5,005,573 A | | 4/1991 | Buchanan |
| 5,911,689 A | * | 6/1999 | Smith et al. ................... 600/310 |
| 6,110,106 A | * | 8/2000 | MacKinnon et al. ......... 600/181 |
| 6,886,964 B2 | * | 5/2005 | Gardiner et al. ............. 362/276 |
| 7,824,395 B2 | * | 11/2010 | Chan et al. ..................... 606/10 |
| 2002/0049389 A1 | * | 4/2002 | Abreu ........................... 600/558 |

(Continued)

FOREIGN PATENT DOCUMENTS

WO  WO-2005/120150 A2  12/2005
WO  WO-2006/049787 A2  5/2006

OTHER PUBLICATIONS

Supplementary Search Report and Search Opinion of the European Patent Office (EPO) for European Patent Application No. 07795713. 2-1657 / 2029964, Mar. 27, 2014.

*Primary Examiner* — Baisakhi Roy
(74) *Attorney, Agent, or Firm* — K&L Gates LLP (57) ABSTRACT

A system including a medical instrument, a sensor, and a processor module in communication with the sensor. The medical instrument includes a radiation source for transmitting electromagnetic radiation from within a body and through a material in the body. The sensor receives a portion of the electromagnetic radiation transmitted through the material, and the processor module determines at least one characteristic of the material based on the electromagnetic radiation received by the sensor.

18 Claims, 6 Drawing Sheets

(56) References Cited

U.S. PATENT DOCUMENTS

| | | | |
|---|---|---|---|
| 2002/0058884 A1* | 5/2002 | Burbank | A61B 17/00491 |
| | | | 600/564 |
| 2002/0127563 A1* | 9/2002 | Salafsky | 435/6 |
| 2003/0125616 A1* | 7/2003 | Black | A61N 5/1048 |
| | | | 600/407 |
| 2004/0127776 A1* | 7/2004 | Walker et al. | 600/310 |
| 2004/0147034 A1* | 7/2004 | Gore | A61B 5/14514 |
| | | | 436/95 |
| 2005/0101824 A1* | 5/2005 | Stubbs | A61N 5/1015 |
| | | | 600/3 |
| 2005/0131500 A1* | 6/2005 | Zalesky | A61M 25/1011 |
| | | | 607/89 |
| 2005/0215871 A1* | 9/2005 | Feldman et al. | 600/309 |
| 2006/0217692 A1* | 9/2006 | Neuberger | 606/12 |
| 2006/0241396 A1* | 10/2006 | Fabian et al. | 600/424 |
| 2007/0161884 A1* | 7/2007 | Black | A61B 5/0031 |
| | | | 600/407 |
| 2008/0208177 A1* | 8/2008 | Mrochen et al. | 606/5 |

* cited by examiner

SYSTEM AND METHODS FOR ILLUMINATING MATERIALS

CROSS-REFERENCE TO RELATED APPLICATIONS

This application is a U.S. national stage application, filed under 35 U.S.C. §371, of International Patent Application No. PCT/US2007/013157, which was filed on Jun. 4, 2007, and which claims priority to U.S. Provisional Patent Application No. 60/810,339, which was filed on Jun. 2, 2006.

TECHNICAL FIELD OF THE INVENTION

This application is directed generally and in various embodiments to systems and methods for illuminating materials, such as materials contained within a human or animal body, to enable visualization of the materials and/or to provide a therapeutic effect thereto.

BACKGROUND

During the performance of invasive surgeries such as lipoplasty procedures, the ability to optimally position and operate surgical instruments such as cannulas and the like within the patient's body is critical to a successful outcome. Surgeons performing these procedures must be able to approximate and visualize the location of a variety of bodily features (e.g., muscles, fat deposits, etc.) that may not be amenable to direct observation. Although devices for accurately imaging the interior of the body such as X-ray and MRI devices are well-known, such devices are large, require specialized personnel to operate, and typically cannot be practically used for the real-time visualization of such procedures. Accordingly, surgeons must often rely upon experience and/or empirical observation to determine proper instrument placement and the locations of bodily features.

SUMMARY

In one general respect, this application discloses a system including a medical instrument, a sensor, and a processor module in communication with the sensor. The medical instrument includes a radiation source for transmitting electromagnetic radiation from within a body and through a material in the body. The sensor receives a portion of the electromagnetic radiation transmitted through the material, and the processor module determines at least one characteristic of the material based on the electromagnetic radiation received by the sensor.

In another general respect, this application discloses a system including a radiation source, a medical instrument, and a processor module in communication with the sensor. The radiation source is positioned external to a body and transmits electromagnetic radiation through a material in the body. The medical instrument includes a sensor for receiving a portion of the electromagnetic radiation from within the body, and the processor module determines at least one characteristic of the material based on the electromagnetic radiation received by the sensor.

In another general respect, this application discloses a medical instrument including a radiation source for transmitting electromagnetic radiation from within a body and through a material in the body. The radiation source is configured such that at least a portion of the electromagnetic radiation passing through the material is emitted from an outer surface of the body.

In another general respect, this application discloses a method for characterizing a material within one of a human body and an animal body. The method includes transmitting electromagnetic radiation through a material in a body, wherein the electromagnetic radiation is transmitted from within the body, receiving a portion of the electromagnetic radiation transmitted by the radiation source through the material, and determining at least one characteristic of the material based on the received electromagnetic radiation.

DESCRIPTION

FIGS. 1A-1C, 5A, 5B, and 6 illustrate a system 5 according to various embodiments of the present invention. As discussed below, the system 5 may be used to illuminate one or more materials contained within a human or animal body so that the material(s) may be located, visualized, identified, differentiated, monitored and/or otherwise assessed by a user of the system 5. Illuminated materials may generally include any bodily material, such as, for example, tissues (e.g., skin tissues, adipose tissues, heart tissues, bone tissues, etc.) and fluids (e.g., blood), as well as non-bodily materials present in the body, such as, for example, injected fluids (e.g., tumescent fluids) or medical devices (e.g., artificial joints, pins, etc.).

Figure 1A:
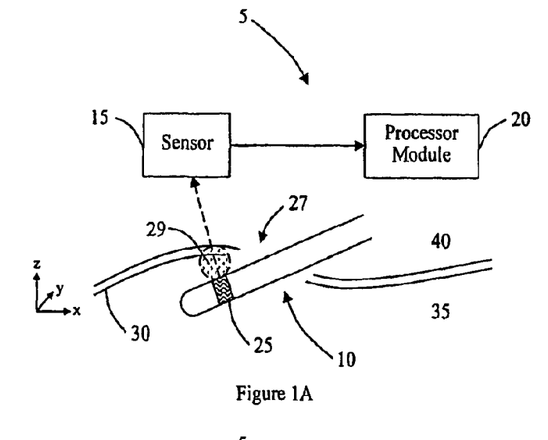
FIGS. 1A-1D illustrate system and instrument configurations according to various embodiments of the present invention.
Figure 5A:
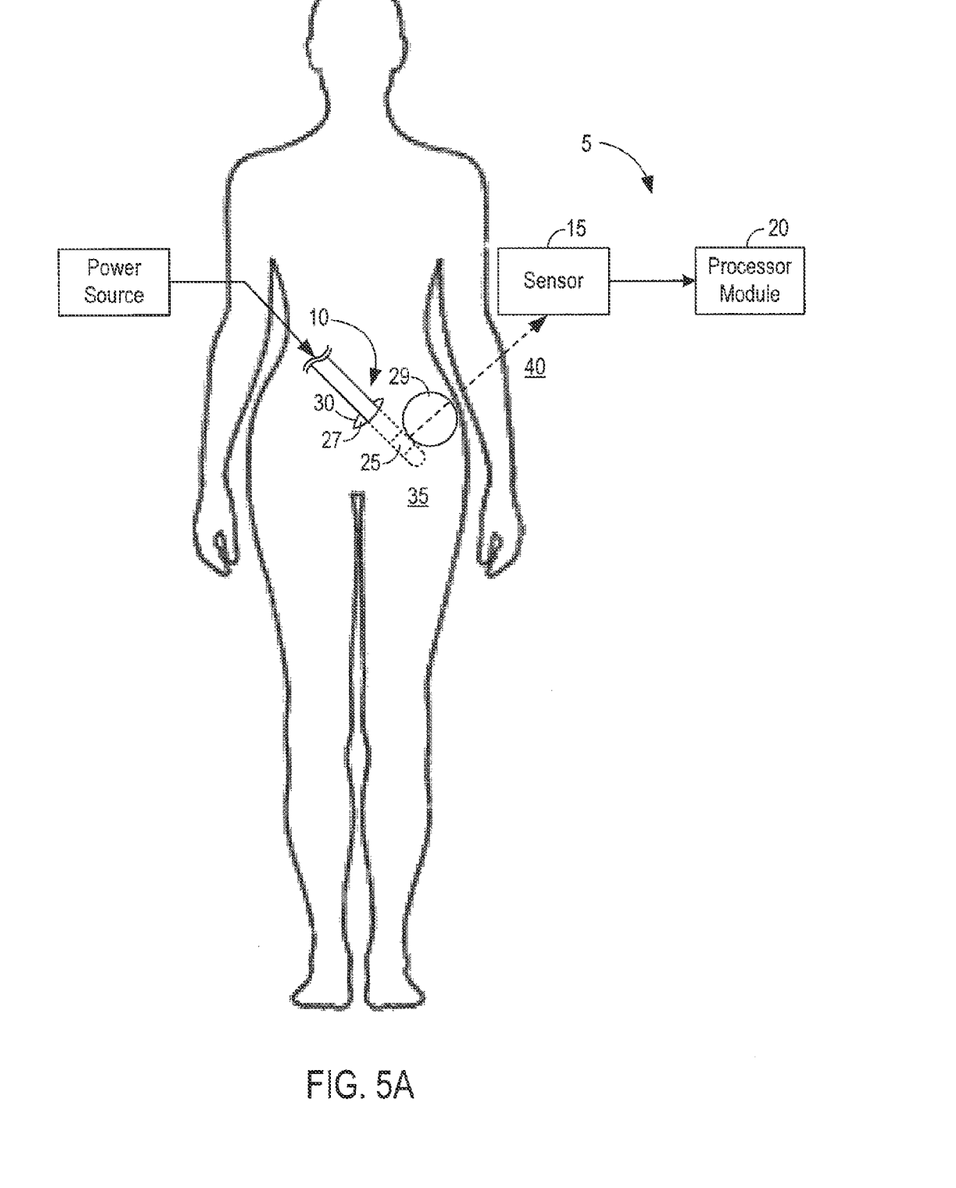
FIGS. 5A and 5B are schematic diagrams further illustrating system and instrument configurations according to the embodiments of the present invention shown in FIGS. 1A and 1B, respectively.
Figure 6:
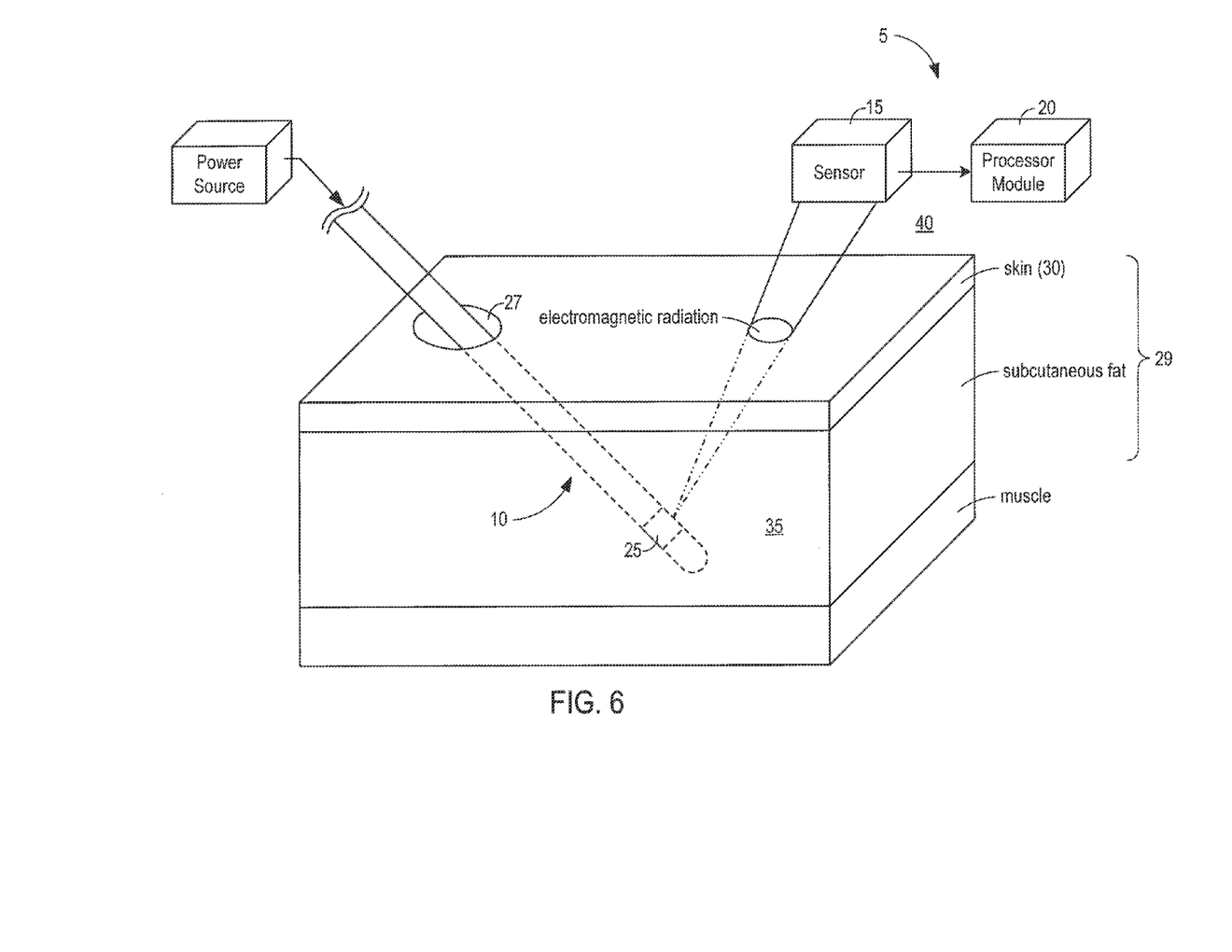
FIG. 6 is a schematic diagram further illustrating system and instrument configurations according to the embodiment of the present invention shown in FIG. 1A.

With reference to FIGS. 1A, 5A, and 6, the system 5 comprises a medical instrument 10, a sensor 15, and a processor module 20. The medical instrument 10 comprises a radiation source 25 for transmitting electromagnetic radiation. In use, a portion of the instrument 10, including the radiation source 25, is inserted into an interior region 35 of a body via a suitable opening 27, such as an incision formed in the skin 30 or a natural orifice. The interior region 35 includes, for example, organ integument or a cavitary space within the body. As shown in FIGS. 1A, 5A, and 6, the sensor 15 may be positioned at a region 40 exterior to the body and receive a portion of the electromagnetic radiation transmitted by the radiation source 25 via one or more materials 29 disposed between the radiation source 25 and the sensor 15. The processor module 20 may be in communication with the sensor 15 and determine at least one characteristic of the material(s) 29 based on electromagnetic radiation received by the sensor 15. As discussed below, such characteristics may include, for example, a composition of the material(s) 29 (e.g., bodily tissue and fluid types forming the material(s) 29), a dimension of the material(s) 29 (e.g., a thickness, area, or volume of the material(s) 29), an arrangement of the material(s) 29 (e.g., an image or other indication of the relative positions of bodily tissues and fluids forming the material(s) 29), a location of the material(s) 29 (e.g., the physical coordinates of the material(s) 29 relative to a fixed reference point), and a movement of the material(s) 29. Due to the positions of the radiation source 25 and the sensor 15 within the interior and exterior regions 35 and 40, respectively, the embodiments of FIGS. 1A, 5A, and 6 represent a "retro-illumination" or "rear lighting" configuration. For such configurations, the material(s) 29 typically includes a portion of the skin 30.

Figure 1B:
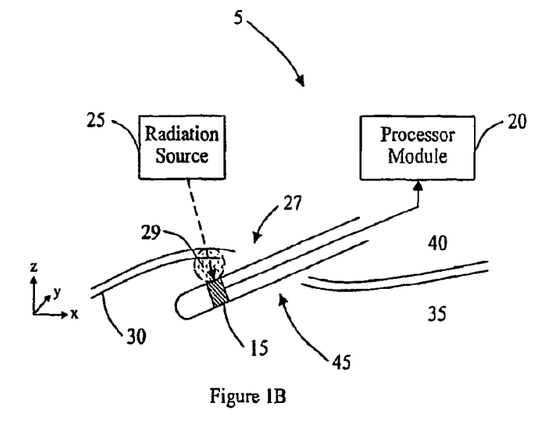
Figure 5B:
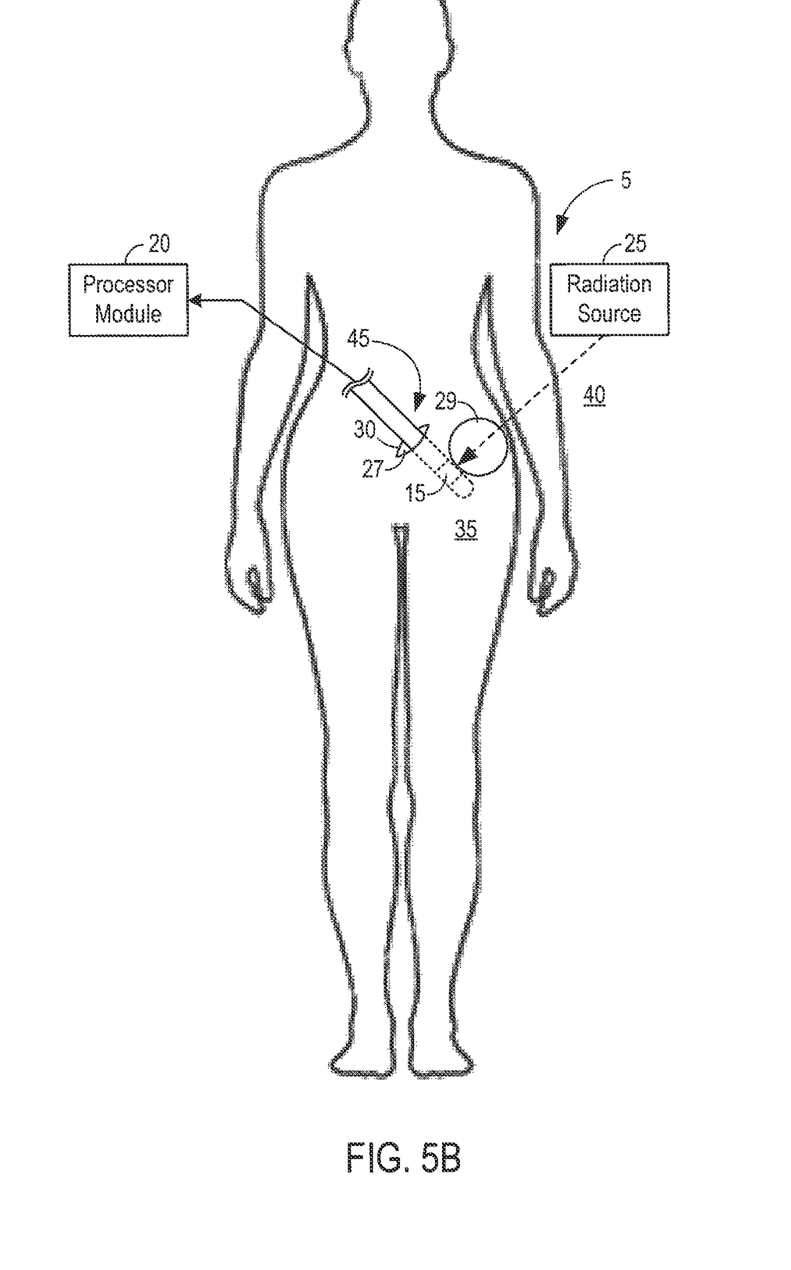

FIGS. 1B and 5B depict an alternative configuration of the system 5 according to various embodiments of the present invention. As shown, the system 5 includes a medical instrument 45 comprising the sensor 15. The radiation source 25 is positioned at the exterior region 40, and the instrument 45 is configured such that the sensor 15 may be inserted within the interior region 35 to receive electromagnetic radiation transmitted via the material(s) 29. According various embodiments, the instrument 45 may be implemented as a known medical device configured to perform one or more functions within the interior region 35 apart from or in conjunction with receiving electromagnetic radiation. According to various embodiments, for example, the instrument 45 may be implemented as a cannula, a catheter, forceps, a cutting instrument, a suction device, or an energy-emitting device for affecting tissue (e.g., an ultrasonic or microwave device). In other embodiments, the instrument 45 may be designed for receiving electromagnetic radiation only.

Figure 1C:
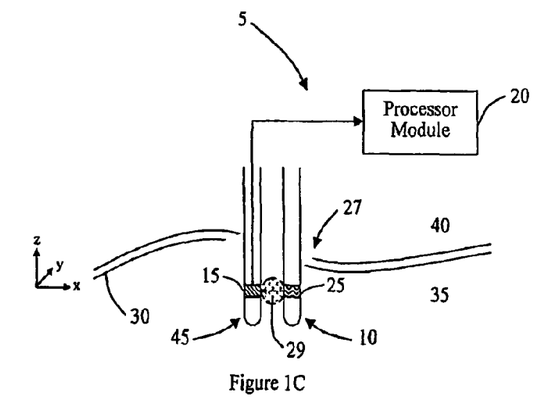

FIG. 1C depicts another alternative configuration of the system 5 according to various embodiments wherein both the radiation source 25 and the sensor 15 are inserted into the interior region 35. According to such embodiments, the system 5 may comprise a medical instrument 45 to which the sensor 15 is attached for facilitating sensor 15 insertion and positioning. The configuration of FIG. 1C may be particularly useful where the material(s) 29 of interest is not sufficiently close to the exterior region 40. In such cases, the configurations of FIGS. 1A-1B, 5A, 5B, and 6 may result in an unacceptably large portion of non-specific material(s) 29 between the radiation source 25 and the sensor 15. The ability to insert and independently position both the radiation source 25 and the sensor 15 addresses this problem and increases the user's ability to target material(s) 29 at deeper positions within the interior region 35.

Figure 1D:
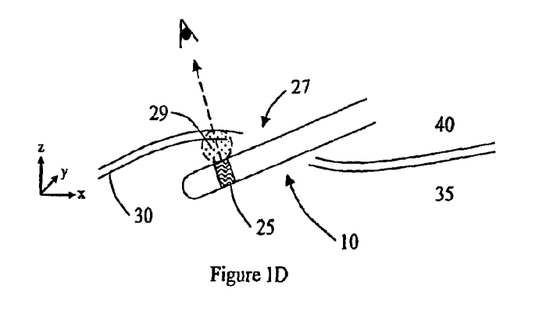

Although the instrument 10 is intended to be used in conjunction with other components of the system 5 as described in the exemplary embodiments of FIGS. 1A, 5A, 6, and 1C above, it will be appreciated that the instrument 10 may also be used apart from the system 5 for purposes of assessing the illuminated material(s) 29 with the naked eye. As shown in the configuration of FIG. 1D, for example, electromagnetic radiation transmitted by the radiation source 25 (e.g., visible light) may be transmitted through one or more material(s) 29 and directly viewed by a user of the instrument 10. Based on the intensity of light emitted from the skin 30, the user may be able to visually determine, for example, the relative position of the instrument 10 within the interior region 35. Additionally, the emitted light may enable the user to visually assess the composition of the illuminated material(s) 29 and various features contained therein.

It will be appreciated that embodiments of the system 5 of FIGS. 1A-1C, 5A, 5B, and 6 are particularly well-suited for performing in vivo analysis of bodily materials. The system 5 may also be used for ex vivo analysis of bodily material in vitro.

Figure 2:
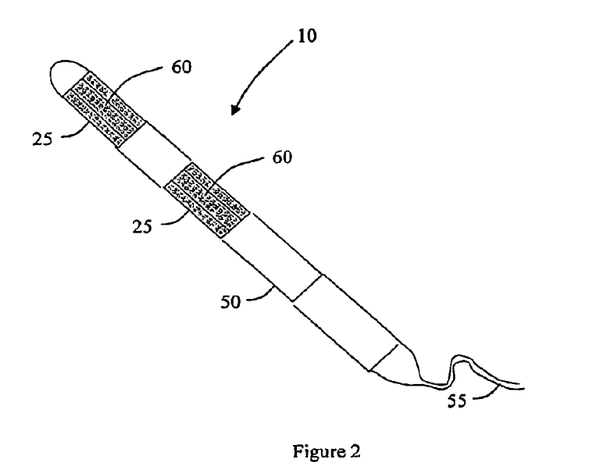
FIG. 2 illustrates a medical instrument for use with the configurations of FIGS. 1A-1D according to various embodiments of the present invention.

FIG. 2 illustrates a medical instrument 10 for use with the configurations of FIGS. 1A, 5A, 6, 1C, and 1D according to various embodiments of the present invention. In certain embodiments and as shown, the medical instrument 10 may be designed for illumination only and provide no additional functionality. In such embodiments, the instrument 10 may comprise a body member 50 formed in the shape of a probe and having a distal end configured to accommodate the radiation source 25. The distal end may also be of a shape suitable for insertion and positioning within the interior region 35 via the opening 27. The instrument 10 may further comprise a power cable 55 for supplying power from an external power source (not shown) to operate the radiation source 25. According to other embodiments, the medical instrument 10 may be implemented as a known medical device configured to perform one or more functions within the interior region 35 apart from or in conjunction with the illumination of the material(s) 29. According to various embodiments, for example, the medical instrument 10 may be implemented as a cannula, a catheter, forceps, a cutting instrument, a suction device, or an energy-emitting device for affecting tissue (e.g., an ultrasonic or microwave device). In such embodiments, the instrument 10 may comprise a distal end or other part configured for insertion into the interior region 35 to which the radiation source 25 may be attached.

Figure 3A:
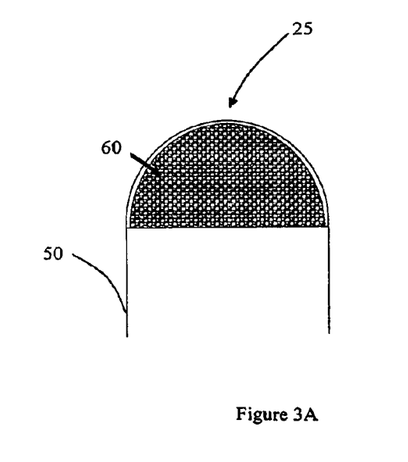
FIGS. 3A-3B illustrate configurations of a radiation source of the medical instrument of FIG. 2 according to various embodiments of the present invention.
Figure 3B:
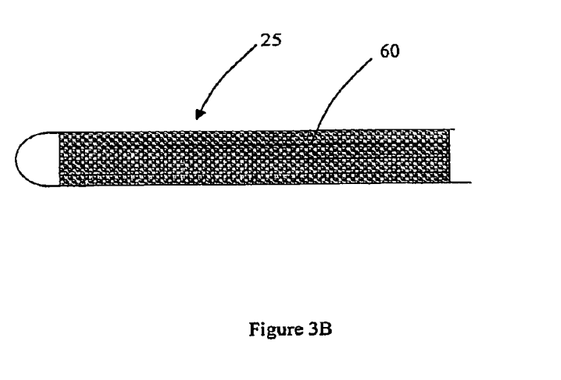

According to various embodiments, the radiation source 25 comprises one or more light-emitting diodes (LEDs) 60 for generating electromagnetic radiation. In one embodiment and as shown in FIG. 2, the radiation source 25 may comprise a plurality of LEDs 60 circumferentially arranged about the distal end of the instrument 10 such that electromagnetic radiation is transmitted uniformly in a radial direction with respect to the longitudinal axis of the instrument 10. The LEDs 60 may be grouped into one or more segments so as to provide the necessary radiation pattern along the longitudinal axis of the instrument 10. For example, as shown in FIG. 2, the LEDs 60 may be grouped into two segments, with each segment capable of being operated separately or in conjunction with the other. The radiation source 25 in general may include one or more separate segments that perform cooperatively. In certain embodiments and as shown in FIG. 3A, the radiation source 25 may additionally or alternatively comprise LEDs 60 arranged upon the distal tip of the instrument 10. Furthermore, although the radiation source 25 of the embodiments of FIG. 2 and FIG. 3A is shown positioned on the distal portion of the instrument 10, it will be appreciated that the radiation source 25 may be extended to include a proximal portion of the instrument 10, as shown in FIG. 3B. It will be appreciated that the radiation sources 25 configurations of FIG. 2 and FIGS. 3A-3B are provided by way of example only and that other suitable radiation source 25 geometries and configurations may be used instead.

According to various embodiments, the LEDs 60 of the radiation source 25 may be selected such that the radiation source 25 transmits electromagnetic radiation within the visible spectrum and/or the infrared (IR) spectrum. In one such embodiment, the LEDs 60 may be selected such that the radiation source 25 transmits substantially monochromatic electromagnetic radiation. In other embodiments, the LEDs 60 may be selected such that the radiation source 25 transmits polychromatic electromagnetic radiation. For example, the radiation source 25 may include LEDS for transmitting both orange and red wavelengths. In such embodiments, the number of LEDs at each wavelength may be selected in accordance with a desired ratio (e.g., the ratio of orange LEDS to red LEDs may be selected as 2:1). According to various embodiments, the LEDs 60 may be implemented using any suitable type of LED package, such as, for example, a conventional bullet package or a SMT package.

To evaluate the transmittance of electromagnetic radiation through tissue, specimens prepared from abdominoplasty extracts were transilluminated with individual LEDs, each having an output wavelength in the visible or IR spectrums (see Table 1 below). The extracts were obtained from a morbidly obese human and contained the intact epidermis layer and all original interstitial tissue, including a high percentage of superficial fat and deep fat pockets. The unaltered specimens were 3-cm in thickness. Each specimen was transilluminated from its deep surface at each output wavelength, and the amount of light emerging through the outer layer (epidermis) was visually quantified and compared to the amount of light incident on the deep surface to estimate the transmittance of light through the specimen. Light in the IR spectrum was visually quantified using night vision equipment. Transmittance at each output wavelength was similarly estimated through dissected 2-cm and 1-cm specimen thicknesses and through the outer epithelial layer (including the epidermis and the dermis) after its dissection and removal from the underlying superficial fat layer. The estimated transmittances at each wavelength for each specimen thickness and the outer epithelial layer are presented in Table 1 below.

nm wavelengths were not visible and appeared to be absorbed entirely. Visibility of the 880 nm wavelength was good with an estimated transmittance of 45%, and the 940 nm wavelength was visible with an estimated transmittance of 30%.

At the 1-cm thickness, all wavelengths exhibited at least some degree of visibility. The 465 nm wavelength was barely visible with an estimated transmittance of 10%, and the 510 nm wavelength was visible with an estimated transmittance of 15%. The 580 nm wavelength exhibited good visibility with an estimated transmittance of 50%, and the 640 nm and mixed wavelengths were brightly visible, with an estimated transmittance of 70% for each. Visibility of the 880 nm wavelength was bright with and estimated transmittance of 55%, and visibility of the 940 nm wavelength was good with an estimated transmittance of 45%.

Through the outer epithelial layer, all wavelengths exhibited at least some degree of visibility. The 580 nm, 640 nm, mixed, and 880 nm wavelengths exhibited the least absorbance and were brightly visible on the outer surface of the layer, with estimated transmittances of 65%, 80%, 80% and 70%, respectively.

Figure 4:
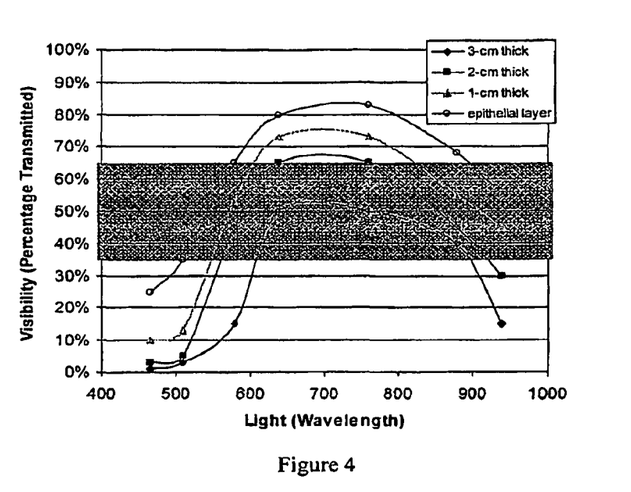
FIG. 4 is a graph of the estimated transmittances of Table 1 as a function of wavelength for each specimen thicknesses and the outer epithelial layer.

FIG. 4 is a graph of the estimated transmittances of Table 1 as a function of wavelength for each specimen thicknesses and the outer epithelial layer. Although the constituent wavelengths of the mixed light were distributed across the visible spectrum, a 780 nm wavelength was used in FIG. 4 to represent the mixed light, as this wavelength is near the limit of visible light.

For the purpose of visually assessing tissue features, it was determined that the preferred wavelengths for transil-

TABLE 1

Estimated Transmittance through Dissected Layers

| | 3 cm | 2 cm | 1 cm | Epithelial layer |
|---|---|---|---|---|
| ~465 nm (Blue) | NV | NV | BV (~10%) | V (~25%) |
| ~510 nm (Green) | NV | NV | V (~15%) | VG (~30%) |
| ~580 nm (Orange) | BV (~15%) | V (~45%) | VG (~50%) | VB (~65%) |
| ~640 nm (Red) | VG (~50%) | VB (~65%) | VB (~70%) | VB (~80%) |
| Mixed (White) | VG (~50%) | VB (~65%) | VB (~70%) | VB (~80%) |
| ~880 nm (IR1) | VG (~40%) | VG (~45%) | VB (~55%) | VB (~70%) |
| ~940 nm (IR2) | BV (~15%) | V (~30%) | VG (~45%) | VB (~55%) |

NV: not visible
BV: barely visible
V: visible
VG: visible good
VB: visible bright At the 3-cm thickness, the 580 nm, 640 nm and mixed wavelengths were visible, with the estimated transmittances of the 640 nm and mixed wavelengths being the highest at 50%. With an estimated transmittance of 15%, the 580 nm wavelength was barely visible. The 465 nm and 510 nm wavelengths were not visible and appeared to be absorbed entirely. Of the IR wavelengths, only the 880 nm wavelength exhibited appreciable transmittance, estimated at 40%. The estimated transmittance of the 940 nm wavelength was 15%. It was observed that the estimated transmittance of visible light increased with increasing wavelength, whereas the estimated transmittance of infrared light decreased with increasing wavelength.

At the 2-cm thickness, the 640 nm and mixed wavelengths exhibited bright visibility, each having an estimated transmittance of 65%. With an estimated transmittance of 45%, the 580 nm wavelength was visible and noticeably brighter compared to that of the 3-cm thickness. The 465 nm and 510 luminating a particular tissue thickness generally corresponded to transmittances in the range of about 35% to 65% (represented by the shaded band in FIG. 4). For transmittances under 35%, the amount of light emerging from the outer layer was barely visible and generally insufficient for visualizing tissue features. For transmittances greater than 65%, the brightness of the light emerging through the outer layer tended to reduce the ability to visually discriminate between different tissue features. Thus, for example, the preferred wavelengths for transilluminating a tissue thickness of 3-cm, based on the corresponding trendline of FIG. 4, are expected to fall within a range of approximately 600-900 nm. By contrast, preferred wavelengths for transilluminating the outer epithelial layer would be expected to fall within ranges of approximately 500-575 nm and 900-940 nm. Thus, the 465 nm and 510 nm wavelengths may be suitable for observing surface and sub-surface features of tissue at depths less than 0.75-cm from the surface.

As noted above, the estimated transmittance values of Table 1 were obtained using abdominoplasty extracts, and it will be appreciated that transmittance values for other tissue types (from humans or animals) may differ from those above for identical values of thickness and wavelength. Thus, for example, whereas the 640 nm and mixed wavelengths may be suitable for transilluminating an abdominoplasty specimen having a 3-cm thickness, these wavelengths may only be suitable for transilluminating lesser thicknesses of other tissue types.

In addition or as an alternative to the use of LEDs for generating electromagnetic radiation in the visible and IR bands as described above, it is contemplated that LEDs for generating other wavelengths of electromagnetic radiation, such as ultraviolet (UV) wavelengths, may also be used.

As an alternative to including LEDs 60 on the instrument 10 as a source of electromagnetic radiation, optical fibers (not shown) may be used to supply electromagnetic energy to the radiation source 25 from an external source (not shown). In such embodiments, characteristics of the electromagnetic radiation may be identical to those described above in connection with the LED-based radiation source 25.

According to various embodiments, the sensor 15 may comprise one or more photodetectors, such as, for example, a photodiode or a CCD array, configured for generating a signal representative of at least one of a wavelength of received electromagnetic radiation and an intensity of received electromagnetic radiation. Other information, such as the spatial distribution of the received electromagnetic radiation, may also be represented by the signal. According to various embodiments, the sensor 15 may comprise an analog-to-digital converter (ADC) for converting the generated signal into a digital format suitable for communication to the processor module 20.

According to various embodiments, the system 5 may further comprise at least one optical element (not shown), such as a lens, for example, disposed between the radiation source 25 and the sensor 15 focusing electromagnetic radiation upon the sensor 1S and reducing any dispersive effects. In certain embodiments, an optical element may be integral to the sensor.

According to various embodiments, the system 5 may further comprise a cone (not shown), an electromagnetic shield (not shown) or similar device located at the exterior region 40 and disposed between the radiation source 25 and the sensor 15. The radiation guide may be configured for capturing electromagnetic radiation transmitted by the radiation source 25 and focusing it towards the sensor 15. Tumescent substances or other substances that improve the transmissibility of electromagnetic radiation through the material(s) 29 may also be utilized. Additionally, tumescent fluids or fluorescent additives or dyes may be used to release absorbed light at a controlled rate, allowing an illuminated region to be observed for a period of time after the radiation source 25 is deactivated or removed.

The temperature of the material(s) 29 may also be regulated by tumescent substances. Heating or cooling of the material(s) 29 may have a positive impact on the energy transmission through the material(s) 29 by increasing accuracy of its corresponding characteristics as determined by the processor module 20.

According to various embodiments, the processor module 20 may comprise any suitable microprocessor-based device configured for determining at least one characteristic of the material(s) 29 based on the signal output by the sensor 15. Although not shown for purposes of clarity, the processor module 20 may comprise components well known in the microprocessor art such as, for example, a processor, one or more random access memory (RAM) units, one or more erasable programmable read-only memory (EPROM) units, an interrupt controller unit, timer and/or clock units, and a number, of general input/output (I/O) ports for receiving and transmitting digital and/or analog signals. The processor module 20 may further comprise a keypad (not shown) or other device for enabling user control of aspects of the processor module operation, and a display (e.g., an LCD screen) for outputting determined characteristics of the material(s) 29 and other information.

According to one embodiment, the processor module 20 may first determine a degree by which the material(s) 29 has attenuated electromagnetic radiation transmitted by the radiation source 25. Using this information, the processor module 20 may next determine a dimension of the material(s) 29 (e.g., a thickness, area, or volume of the material(s) 29). According to another embodiment, the processor module 20 may first determine the spectral content of electromagnetic radiation received by the sensor 15. Utilizing this information, as well as information stored a priori regarding the effect of known materials upon the electromagnetic radiation transmitted by the radiation source 25, the processor module 20 may next determine the composition of the material(s) 29 (e.g., bodily tissue and fluid types forming the material(s) 29). The intensity, spectral content, and other information contained within the signal may also be utilized to determine an arrangement of the material(s) 29 (e.g., an image or other indication of the relative positions of tissues and fluids forming the material(s) 29), a location of the material(s) 29 (e.g., the physical coordinates of the material(s) 29 relative to a fixed reference point), and a movement of the material(s) 29.

In use, the radiation source 25 of FIGS. 1A, 5A, and 6 may be maneuvered inside the interior region 35 and placed into contact with tissue or other features of interest. Aspects of the electromagnetic radiation (e.g., color, intensity, attenuation, etc.) transmitted through the material are uniquely determined by the material's physical properties. For example, fat tissue, muscle tissue and skin tissue may each exhibit a unique light absorption property for a given wavelength of electromagnetic radiation. Such differences are manifested in the signal output by the sensor 15. In this way, the processor module 20 may discern a tissue profile that consists of a 4-cm layer of muscle, beneath a 0.75-cm layer of fat, beneath a 0.25-cm layer of skin, for example. The ability to discriminate between different materials in this manner is particularly useful for ensuring that only a desired material (e.g., adipose tissue of different types) is targeted during a procedure Similarly, for a clinical application performed within the interior region 35 of a human or animal, the radiation source 25 of FIG. 1C may be placed inside a hollow organ (e.g., bladder, stomach, gastrointestinal tract, vessel, etc.) and the sensor 15 placed on the exterior surface of that same organ, or within its regional integument. In a manner similar to that described above, electromagnetic radiation may be transmitted through the organ wall and sensed as it exits the opposite surface. Aspects of the sensed radiation may be used to characterize various features or localized irregularities in the composition of the organ. Additionally, absorption of at least a portion of the radiation by the organ may provide a therapeutic effect for treating disease or other medical defects. In certain embodiments, the absorption of electromagnetic radiation may be enhanced or otherwise affected by the administration of one or more dyes and/or fluorescent materials.

Although the above embodiments of system 5 deal predominantly with bodily material, in vivo (e.g., in a surgical procedure), it will be appreciated that system 5 may also be employed for in vitro analysis of bodily and non-bodily material. Such use may entail analysis of excised tissue or biopsy material to help differentiate between different types of lesions. Such use may also entail analysis of bacterial cultures or food samples in a Petri dish to help determine important characteristics relating to effectiveness of antibiotics or age of material.

One use of the system 5, particularly the configuration of FIGS. 1A, 5A, and 6, is for guiding a surgeon's progress during invasive surgery, such as, for example, a lipoplasty procedure, an organ or cyst removal procedure, or the suture or biopsy of internal organs or tissues. During a lipoplasty procedure, for example, the surgeon benefits by knowing the position of the cannula (or other instrument) with respect to the tissue (e.g., fat, skin, fascia, muscle, etc.) involved. The cannula may include, for example, visible and/or infrared LEDs arranged about its distal end to form a radiation source 25 as discussed above. The LED wavelengths may be based on transillumination requirements at different depths within the integument of a body. For example, the radiation source 25 may include an arrangement of LEDs having wavelengths within the 450-550 nm range for providing retro-illumination of surface features and other features at depths of about 3-cm or less beneath the skin surface. The radiation source 25 may further include an arrangement of LEDs having wavelengths within the 550-680 nm range for providing retro-illumination of tissue at depths of about 2-cm or more beneath the skin surface. For example, LEDs having wavelengths in the orange and red portions of the visible spectrum may be used to retro-illuminate pockets of deep fat, allowing a surgeon to gauge instrument position and depth within the body while simultaneously receiving real-time information regarding the instrument's proximity to greater amounts of adipose cells. Additionally, the distal end may include an arrangement of mixed (white) LEDs for enabling navigation and positioning at depths greater than 3-cm beneath the skin surface.

For procedures requiring multiple instruments, the distal end of each instrument may include one or more of the LEDs arrangements as described above. For example, for a lipoplasty procedure requiring the use of three cannulae, a first cannula for removing a desired volume of deep fat during a first phase of the procedure may include one or more arrangements of LEDs having red and/or white wavelengths. A second cannula including one or more arrangements of LEDs having orange and red wavelengths may be used during a second phase of the procedure to remove superficial fat layers and residual amounts of deep fat. As more fat is removed, the orange wavelengths may become more visible and the brightness of the red wavelengths may increase, indicating to the surgeon that the desired amount of fat has been suctioned. A third cannula including LEDs having blue and green wavelengths may be used during a final phase of the procedure to remove superficial fat layers and fat layers in places of shallow tissue depth (e.g., anterior regions of the arms).

The retro-illumination configuration of FIGS. 1A, 5A, and 6 may also be useful for biopsies and tissue assessment. For example, as a part of early-stage breast cancer screening, the system 5 may be used to detect and characterize tumors or cysts. Additionally, the system 5 may be employed in conjunction with mammograms to provide primary characterization of a tumor or as an adjunctive co-screen to reduce the number of false negatives. The system 5 may also be used in conjunction with diagnostic procedures such as, for example, fine-needle aspirations, ductal lavages, core-needle biopsies and local surgical biopsies. For example, where these methods fail to collect enough tissue because the intended target is missed, enhancing the observable area by retro-illumination may better define the target areas and allow for more selective extraction at multiple points. The retro-illuminating lights (including visible or infrared LEDs) may be integrated on the extraction needle itself.

The retro-illumination configuration of FIGS. 1A and 5A is also suitable for detecting abnormalities on the surface of or within an organ or organ system. In the same way that ultrasound and magnetic resonance may be used for investigating suspicious areas or for uncovering lesions obscured on mammograms, the system 5 may be used to identify problematic areas undetectable on a mammogram. For example, as a part of the "work-up" process of breast cancer diagnosis, insertion under the breast of a small instrument including an arrangement of visible and/or IR LEDs for retro-illuminating local areas of interest may augment both screening and diagnostic mammographies. The probe may be inserted and positioned, for example, on the posterior surface of the breast (along the pectoralis muscle fascia) or within the breast itself. Additionally, retro-illumination may be employed to better resolve the shape and boundary delineations of certain tissue areas of interest for purposes of enhancing a diagnostic mammography. The radiologist may interpret mammograms with the aid of images and/or other information provided by retro-illumination of the tissue. The morphology of an unidentified formation, existing on the surface of the breast or within, may help the radiologist screen for cancerous tumors or cysts. This may enable a more accurate assessment of tumors and cysts and reduce the number of false negative cases.

Additionally, the retro-illumination configuration of FIGS. 1A and 5A may be used to analyze internal organs (e.g., kidneys, liver) by directly inserting a lighted probe to a desired depth within the organ integument. The configuration of FIG. 1C may similarly be used to analyze internal organs by inserting the instruments 10, 45 such that the materials of interest are suitably positioned between the radiation source 25 and the sensor 15. Transmission of light through the organ may also be used to provide therapeutic effects.

The retro-illumination configuration of FIGS. 1A, 5A, and 6 may also be used in procedures such as lumpectomies in which the surgeon's inability to remove the entire targeted tumor or potentially cancerous area may result in additional growth and subsequent operations. The entire area to be removed may be retro-illuminated using a needle incorporating the radiation source or using a dedicated illumination instrument. The system 5 may also be used during the course of the procedure or at specific intervals so that the surgeon may account for removed tissue before, during and after insertions of the extraction needle.

Another use of the system 5, particularly the configuration of FIG. 1C, is for quantifying the amount of fat removed during a lipoplasty procedure. For example, a sample of material removed during the procedure (including fat and other materials) may be transilluminated to measure the transmittance therethrough. The measured transmittance may then be compared to one or more transmittance values obtained a priori from samples of a material having known fat concentrations. Based on the comparison, a weight-based fat concentration of the transilluminated sample may be calculated. The weight of material removed during the procedure may then be multiplied by calculated fat concentration to quantify the weight of the fat removed during the procedure. The transmittance measurement of the material and the subsequent steps for determining the weight of removed fat may be performed, for example, by the processor module 20.

Retro-illumination and the associated analysis of material may also be useful in therapeutic applications such as irradiation therapy, retro-heating therapy of skin and subcutaneous tissue, muscle, fascia, etc., and chronic pain control. Applications may include creating favorable changes such as skin shrinking, anti-aging, or reversing or controlling adverse processes. Retro-illumination may also be used for assessing internal physiologic processes associated with the aging process (e.g., blood flow changes, etc.).

In conjunction with its uses for assessing bodily materials, embodiments of the system 5 of FIGS. 1A, 5A, and 6 may function as the primary and sole source for visualizing and controlling the surgical procedure. In particular, in cases where the body is retro-illuminated with visible light of sufficient brightness, conventional operating room lighting fixtures (e.g., fluorescent or quartz halogen floorstand or wall mount lights) may be eliminated or reduced in order to provide maximum visibility of the desired internal lighting system of retro-illumination. In this use, the surgeon would be able to conduct all or parts of a surgical procedure relying only on the internal illumination provided by the lighting from the instrument(s) within the cavity.

Whereas particular embodiments of the invention have been described herein for the purpose of illustrating the invention and not for the purpose of limiting the same, it will be appreciated by those of ordinary skill in the art that numerous variations of the details, materials, configurations and arrangement of components may be made within the principle and scope of the invention without departing from the spirit of the invention. The preceding description, therefore, is not meant to limit the scope of the invention.

What is claimed is:

1. A system comprising:
a medical instrument configured for subcutaneous insertion into a body through a surgical incision made through skin, the medical instrument comprising a radiation source for transmitting electromagnetic radiation from within the body, through bodily tissues and/or fluids in the body, and through the skin, wherein a portion of the electromagnetic radiation is sensed external to the skin of the body, and wherein the radiation source is located on or in a distal end of the medical instrument;
a sensor positioned external to the skin of the body for receiving the portion of the electromagnetic radiation transmitted from within the body, through the bodily tissues and/or fluids, and through the skin; and
a processor module in communication with the sensor, wherein the processor module is for determining at least one characteristic of the bodily tissues and/or fluids based on the electromagnetic radiation received by the sensor.

2. The system of claim 1, wherein the medical instrument is selected from the group consisting of: a cannula, a catheter, forceps, a cutting instrument, a suction device, an ultrasonic energy-emitting device, a microwave energy-emitting device, and an energy-emitting device configured for lipoplasty procedures.

3. The system of claim 1, wherein the radiation source transmits substantially monochromatic electromagnetic radiation.

4. The system of claim 1, wherein the radiation source transmits polychromatic electromagnetic radiation.

5. The system of claim 1, wherein the radiation source is for transmitting electromagnetic radiation within at least one of the following electromagnetic spectrums: an ultraviolet (UV) spectrum, an infrared (IR) spectrum, and a visible spectrum.

6. The system of claim 1, wherein the radiation source comprises at least one of the following: a UV light-emitting diode (LED), an IR LED, and a visible LED.

7. The system of claim 1, further comprising one or more optical fibers for supplying electromagnetic energy to the radiation source.

8. The system of claim 1, wherein the sensor comprises one or more photodetectors.

9. The system of claim 1, further comprising at least one optical element disposed between the radiation source and the sensor.

10. The system of claim 1, wherein the sensor is for generating a signal representative of at least one of a wavelength and an intensity of the received electromagnetic radiation, and wherein the sensor is for communicating the signal to the processor module.

11. The system of claim 1, wherein the at least one determined characteristic of the bodily tissues and/or fluids is selected from the group comprising: a composition of the bodily tissues and/or fluids, a dimension of the bodily tissues and/or fluids, an arrangement of the bodily tissues and/or fluids, a location of the bodily tissues and/or fluids, and a movement of the bodily tissues and/or fluids.

12. A medical instrument configured for subcutaneous insertion into a body through a surgical incision made through skin, the medical instrument comprising cannula, a catheter, forceps, a cutting instrument, a suction device, an ultrasonic energy-emitting device, a microwave energy-emitting device, or an energy-emitting device configured for lipoplasty procedures, the medical instrument further comprising:
a radiation source for transmitting electromagnetic radiation from within the body, through bodily tissues and/or fluids in the body, and through the skin,
wherein the radiation source is located on or in the distal end of the cannula, the catheter, the forceps, the cutting instrument, the suction device, the ultrasonic energy-emitting device, the microwave energy-emitting device, or the energy-emitting device configured for lipoplasty procedures; and
wherein the radiation source is configured such that at least a portion of the electromagnetic radiation transmitted through the skin and the bodily tissues and/or fluids is emitted from an outer surface of the skin of the body and received by a sensor positioned external to the skin of the body.

13. A method for characterizing bodily tissues and/or fluids within one of a human body and an animal body, the method comprising:
transmitting electromagnetic radiation through bodily tissues and/or fluids in a body, and through skin, wherein the electromagnetic radiation is transmitted from within the body from a device inserted subcutaneously into the body through a surgical incision made through the skin, and wherein a portion of the electromagnetic radiation is sensed external to the skin of the body, and wherein the radiation transmits from a source located on or in a distal end of the device;

receiving external to the skin of the body the portion of the electromagnetic radiation transmitted through the bodily tissues and/or fluids, and through the skin; and determining at least one characteristic of the bodily tissues and/or fluids based on the received electromagnetic radiation.

14. The method of claim 13, wherein transmitting electromagnetic radiation source includes transmitting electromagnetic radiation within at least one of the following electromagnetic spectrums: a UV spectrum, an IR spectrum, and a visible spectrum.

15. The method of claim 13, wherein determining at least one characteristic of the bodily tissues and/or fluids includes determining at least one characteristic of the bodily tissues and/or fluids based on at least one of a wavelength and an intensity of the received electromagnetic radiation.

16. The method of claim 13, wherein determining at least one characteristic of the bodily tissues and/or fluids includes determining at least one of a composition of the bodily tissues and/or fluids, a dimension of the bodily tissues and/or fluids, an arrangement of the bodily tissues and/or fluids, a location of the bodily tissues and/or fluids, and a movement of the bodily tissues and/or fluids.

17. A system comprising:
a medical instrument configured for subcutaneous insertion into a body through a surgical incision made through skin, the medical instrument comprising a radiation source for transmitting electromagnetic radiation from within the body, through bodily tissues and/or fluids in the body, and through the skin, wherein a portion of the electromagnetic radiation is sensed external to the skin of the body, and wherein the radiation source is located on or in a distal end of the medical instrument;

a sensor positioned external to the skin of the body for receiving the portion of the electromagnetic radiation transmitted from within the body, through the bodily tissues and/or fluids, and through the skin; and a processor module in communication with the sensor, wherein the processor module is for determining at least one characteristic of the bodily tissues and/or fluids based on the electromagnetic radiation received by the sensor;

wherein the electromagnetic radiation is visible through the skin, providing a surgeon with subcutaneous positioning information of the medical instrument.

18. A method for characterizing bodily tissues and/or fluids within one of a human body and an animal body, the method comprising:

transmitting electromagnetic radiation through bodily tissues and/or fluids in a body, and through skin, wherein the electromagnetic radiation is transmitted from within the body from a device inserted subcutaneously into the body through a surgical incision made through the skin, and wherein a portion of the electromagnetic radiation is sensed external to the skin of the body, and wherein the electromagnetic radiation transmits from a source located on or in a distal end of the device;

receiving external to the skin of the body a portion of the electromagnetic radiation transmitted through the bodily tissues and/or fluids, and through the skin; and determining at least one characteristic of the bodily tissues and/or fluids based on the received electromagnetic radiation;

wherein the electromagnetic radiation is visible through the skin, providing a surgeon with subcutaneous positioning information of the medical instrument.

* * * * *